United States Patent
Fisher et al.

(10) Patent No.: US 8,294,588 B2
(45) Date of Patent: Oct. 23, 2012

(54) BATTERY SYSTEM FOR MRI COMPATIBLE WIRELESS PATIENT MONITOR

(75) Inventors: Stephen Douglas Fisher, Winter Springs, FL (US); Robert A. Harwell, Orlando, FL (US); Kenneth Van Arsdel, Orlando, FL (US)

(73) Assignee: Koninklijke Philips Electronics N.v., Eindhoven (NL)

( * ) Notice: Subject to any disclaimer, the term of this patent is extended or adjusted under 35 U.S.C. 154(b) by 578 days.

(21) Appl. No.: 12/440,027

(22) PCT Filed: May 10, 2007

(86) PCT No.: PCT/US2007/068648
§ 371 (c)(1),
(2), (4) Date: Mar. 5, 2009

(87) PCT Pub. No.: WO2007/134156
PCT Pub. Date: Nov. 22, 2007

(65) Prior Publication Data
US 2010/0191069 A1     Jul. 29, 2010

Related U.S. Application Data

(60) Provisional application No. 60/799,884, filed on May 12, 2006.

(51) Int. Cl.
*G08B 21/00* (2006.01)
*G08C 15/00* (2006.01)
*A61B 5/00* (2006.01)
*G01V 3/00* (2006.01)

(52) U.S. Cl. ............... 340/636.1; 340/870.15; 600/300; 324/322

(58) Field of Classification Search ............... 340/636.1
See application file for complete search history.

(56) References Cited

U.S. PATENT DOCUMENTS

| 7,091,879 | B2 | 8/2006 | Swetlik et al. | |
|---|---|---|---|---|
| 2003/0206019 | A1 | 11/2003 | Boskamp | |
| 2004/0176673 | A1 | 9/2004 | Wahlstrand et al. | |
| 2005/0113676 | A1 | 5/2005 | Weiner et al. | |
| 2005/0156565 | A1 * | 7/2005 | Chien | 320/112 |
| 2005/0273001 | A1 * | 12/2005 | Schmainda et al. | 600/411 |
| 2006/0241384 | A1 | 10/2006 | Fisher et al. | |
| 2006/0247512 | A1 | 11/2006 | Harwell et al. | |
| 2008/0272786 | A1 * | 11/2008 | Luedeke et al. | 324/322 |
| 2008/0312852 | A1 * | 12/2008 | Maack | 702/63 |

FOREIGN PATENT DOCUMENTS
WO    2006048838 A1    5/2006

* cited by examiner

*Primary Examiner* — George Bugg
*Assistant Examiner* — Jack Wang

(57) ABSTRACT

A patient monitoring system detects physiological signals from a patient during an MRI examination. The patient monitoring system wirelessly transmits data associated with the physiological signals to a remote base unit. The wireless transmission of data is carried out in a manner to not be disruptive to the MRI examination. The patient monitoring system has a removable, MRI magnet compatible battery.

22 Claims, 2 Drawing Sheets

BATTERY SYSTEM FOR MRI COMPATIBLE WIRELESS PATIENT MONITOR

CROSS-REFERENCE TO RELATED APPLICATIONS

This application claims the benefit of U.S. Provisional Application 60/799,884, filed May 12, 2006, the disclosure of which is incorporated herein by reference.

STATEMENT REGARDING FEDERALLY SPONSORED RESEARCH OR DEVELOPMENT

Background of the Invention

The present invention relates generally to electronic patient monitors and, in particular, to a wireless patient monitor suitable for use in the severe electromagnetic environment of a magnetic resonance imaging (MRI) machine.

Magnetic resonance imaging allows images to be created of soft tissue from faint electrical resonance signals (NMR signals) emitted by atomic nuclei of the tissue. The resonance signals are generated when the tissue is subjected to a strong magnetic field and excited by a radio frequency pulse.

The quality of the MRI image is in part dependent on the quality of the magnetic field, which must be strong and extremely homogenous. Ferromagnetic materials are normally excluded from the MRI environment to prevent unwanted magnetic forces on these materials and distortion of the homogenous field by these materials.

A patient undergoing an MRI "scan" may be received into a relatively narrow bore, or cavity in the MRI magnet. During this time, the patient may be remotely monitored to determine, for example, heartbeat, respiration, temperature, and blood oxygen. A typical remote monitoring system provides "in-bore" patient sensors on the patient connected by electrical or optical cables to a base unit outside of the bore. Long runs of these optical or electrical cables can be a problem because they are cumbersome and can interfere with access to the patient and free movement of personnel about the magnet itself.

Co-pending U.S. patent application Ser. No. 11/080,958, filed Mar. 15, 2005 and Ser. No. 11/080,743 filed Mar. 15, 2005, assigned to the assignee of the present invention and hereby incorporated by reference, describe a wireless patient monitor that may be positioned near the patient to provide real-time monitoring of patient physiological signals. The inventions described in these applications overcome problems of the electrically noisy environment of MRI by using combined diversity techniques including: frequency diversity, antenna location diversity, antenna polarization diversity, and time diversity in the transmitted signals. The quality of the signals is monitored to select among diverse pathways, dynamically, allowing low error rates and high bandwidth at practical transmission power.

While wireless patient sensors offer considerable advantages for use in monitoring patients in the MRI environment, the elimination of wires connecting the patient sensors to a base unit outside the MRI machine (the latter which is normally connected to a power line) raises the problem of providing power to the patient sensor. This is particularly a problem for patient sensors that employ electromechanical devices such as pumps and motors, which can require significant amounts of power.

Placing batteries in the patient sensor is one solution, but many conventional batteries are unsuitable for use in a patient sensor in the MRI machine because of their weight and potential for leakage. Moreover, batteries are generally placed in relative proximity to the circuitry to which they supply power. Patient sensors used with an MRI machine must be shielded against radio frequency interference to operate properly. As such, to reduce the size and simplify the construction of a patient sensor, the battery and the operational circuitry are contained within a common and electrically shielded housing. However, providing a shielded housing for the patient sensor that can be readily opened for the replacement of the batteries and then sealed in a manner that protects the internal circuitry from radio frequency interference can be difficult.

During the scanning procedure the patient sensor is inaccessible and therefore batteries that become exhausted during a scan may require termination of the scan, which can waste valuable time on the MRI machine. Scheduled regular replacement of the batteries can be used to address this problem, but requires continuous attention of staff and inevitably involves replacing or recharging some batteries that still have additional life.

BRIEF SUMMARY OF THE INVENTION

The present invention provides a wireless patient sensor having a battery pocket that houses a battery in such a manner to isolate the battery from operational circuitry that is powered by the battery. The operational circuitry is contained within a shielded portion of the housing whereas the battery pocket is contained within a portion that is not shielded from radio frequency interference. This construction is believed to avoid the problems associated with constructing an electrically tight housing that is repeatedly opened and closed while retaining electrical shielding integrity.

Therefore, in accordance with one aspect, the present disclosure includes a wireless patient monitoring system operative with an MRI machine during an MRI examination. The monitoring system has a housing supporting an antenna for wireless transmission of data associated with physiological signals acquired from a patient during the MRI examination. First and second interior portions are defined within the housing, wherein the first interior portion is electrically isolated from the second interior portion. Circuitry is disposed in the first interior portion and a battery substantially free from ferromagnetic components is disposed in the second interior portion.

In accordance with another aspect of the present disclosure, a wireless patient sensor operative with an MRI machine during an MM examination is presented. The sensor includes a housing having an interior volume and a chamber disposed within a first portion of the interior volume and defined by electrically conductive walls. A shielded circuitry housing is disposed within a second portion of the interior volume and a battery pocket is disposed within a third portion of the interior volume and is electrically isolated from the chamber. The patient sensor further includes electrical connections between circuitry contained within the shielded circuitry housing and the battery pocket through the chamber.

According to a further aspect of the present disclosure, a method is disclosed that includes determining a battery charge of a patient sensor that has been commissioned for use during a scheduled MRI examination. The battery charge of the patient sensor is compared to a minimal charge value required for patient monitoring during the prescribed MRI examination. If the charge of the battery is below the minimal charge value, a signal is wirelessly transmitted to an operator indicating that the commissioned patient sensor lacks sufficient battery charge to be used for the scheduled MRI examination.

Various other features, objects and advantages of the present invention will be made apparent from the following detailed description and the drawings.

BRIEF DESCRIPTION OF THE FIGURES

The drawings illustrate one preferred embodiment presently contemplated for carrying out the invention.

In the drawings.

DETAILED DESCRIPTION OF THE PREFERRED EMBODIMENT

The present invention will be described with respect to the wireless acquisition and transmission of physiological data to a remote base unit that is operative in the magnetic field generated by an MRI magnet. However, it is understood that the present invention may also be useful in other applications involving high-flux magnetic fields.

Figure 1:
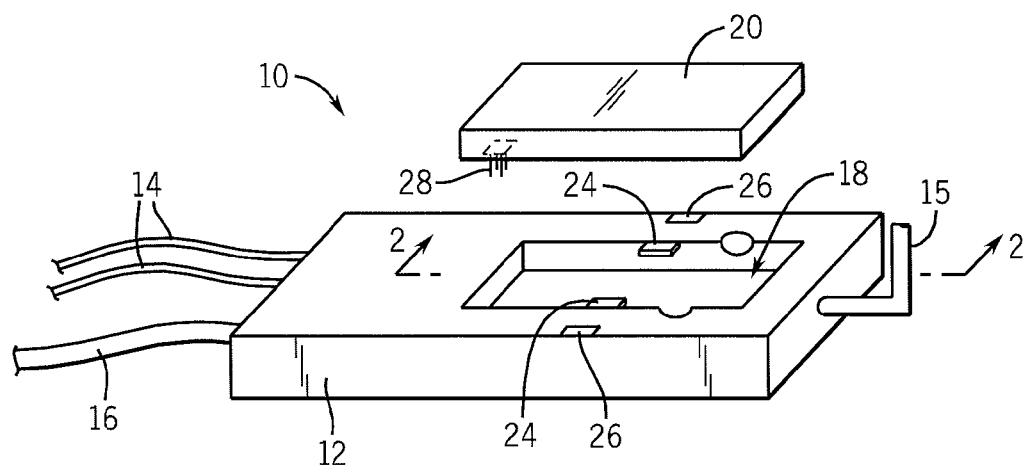
FIG. 1 is an exploded perspective view of a wireless patient sensor of the present invention showing a smart battery positioned above a battery pocket.

Referring now to FIG. 1, the present invention provides a wireless patient sensor 10 having housing 12 providing radio frequency shielding to internal circuitry (not shown in FIG. 1). The housing 12 supports an external antenna 15 and receives external monitoring leads 14 for collecting physiological signals. In some embodiments, the housing may further provide a connection to a hose 16, for example, providing a source of controlled air pressure for inflating a cuff for non-invasive blood measurements or sampling respiration gases or the like. Additional details on the construction of the patient sensor 10 may be found in the co-pending applications, referenced herein, assigned to the assignee of the present invention, and hereby incorporated by reference.

Figure 2:
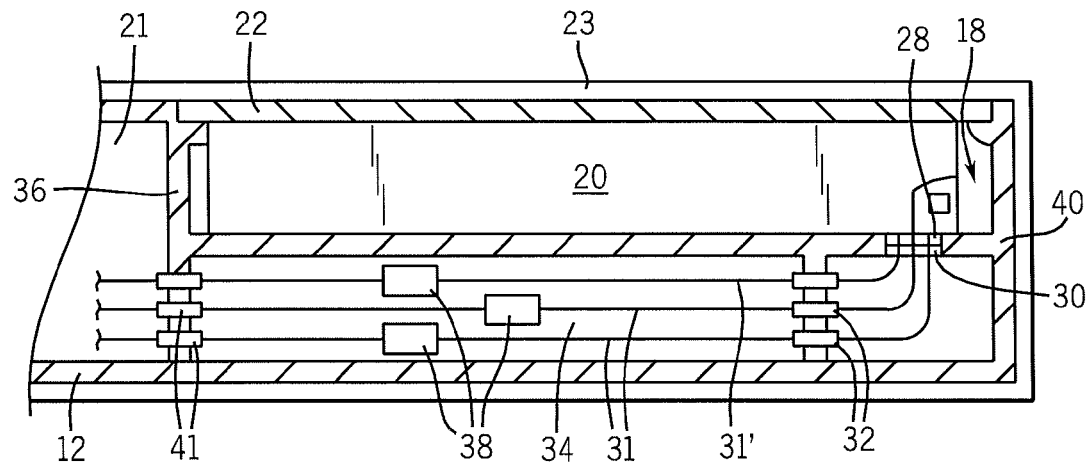
FIG. 2 is a cross-sectional view of FIG. 1 along lines 2-2 showing the radio frequency shielding of power and data lines connecting the battery to the circuitry of the patient sensor.

Referring to FIGS. 1 and 2, the outer walls of the housing 12 may form a pocket 18 to receive all or part of a lithium ion rechargeable smart battery 20. Smart batteries 20 of this type are well known in the art and include integrated circuitry that can identify the type of battery and/or the capacity of the battery and that can monitor the batteries usage and likely reserved capacity. The lithium ion smart battery 20 is substantially free from ferromagnetic components to resist magnetic attraction by the MRI magnet.

The pocket 18 may be electrically isolated from an interior 21 of the housing 12 by substantially continuous and electrically conductive walls 40 of the housing 12. In embodiments in which the battery 20 may fit wholly within the pocket 18, the battery 20 may be covered by a cover 22 (shown in FIG. 2) or may be held by latch fingers 24 (shown in FIG. 1). In this latter embodiment, the latch fingers 24 extending over the top of the pocket 18 when the battery 20 is in place in the pocket 18 and are releasable by spring loaded buttons 26 or the like. Shown also in FIG. 2 is an outer enclosure 23 of insulating material, such as a polymer, that may provide an opening aligned with the pocket 18 or which may cover the pocket 18 allowing access to the battery 20 by disassembly of the enclosure 23.

In each of these embodiments, the battery pocket 18 need not be shielded from radio frequency interference eliminating the need for electrically shielded pocket covers that may be difficult to use or unreliable in daily use. Instead, the present invention provides for a connection with terminals 28 on the battery 20 that blocks not only radio frequency interference coming along the power leads from the terminals 28 but also radio frequency interference that can affect reading of the smart data obtainable from the smart battery 20.

Figure 3:
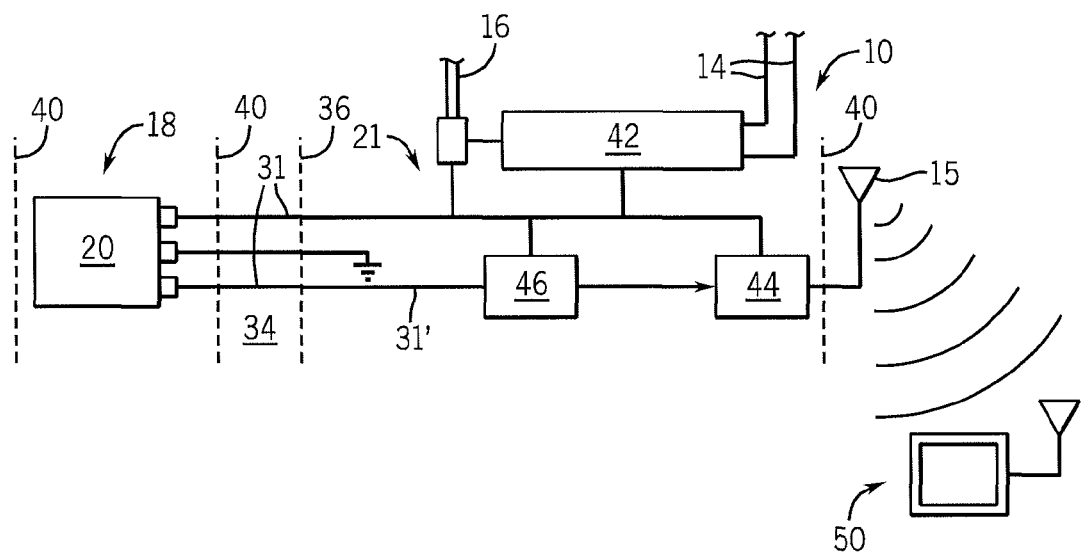
FIG. 3 is a schematic block-diagram of the circuitry of the patient sensor of FIG. 1 in communication with a base unit.

Referring now to FIGS. 1, 2 and 3, the bottom of the pocket 18 may provide a connector 30 interfacing with terminals 28 of the battery 20 and provide leads 31 for conducting power from the battery 20 and lead 31' (referenced to one of leads 31) for providing data from the battery 20 on battery type, capacity, remaining charge, and the like. The leads 31 and 31' pass through a series of feed through capacitors 32 in one wall of a quiet box 34, the latter which provides a volume that is wholly enclosed by conductive walls 36 which may include some of the walls 40 of the housing 12 but which is nevertheless electrically isolated from the interior 21 of the housing 12.

Within the quiet box 34, the leads 31 and 31' from connector 30 are received by other filter elements 38 (e.g., radio frequency chokes) after which they pass through a second set of feed through capacitors 41 through a shared wall 36 of housing 12 into the interior 21 of the housing 12. The filter elements 38 are selected to provide low pass filters for the power leads 31 with a break point (e.g., less than ten Hertz), and a band pass filter for the data lead 31' narrowly centered on the power spectrum for normal data communication rate for the data lead 31'.

Referring now to FIG. 3, within the housing interior 21, the power leads 31 provide power and ground signals to control circuitry 42, transmitter circuitry 44, and battery status circuitry 46, which may be realized as separate circuits or integrated together, for example, using a field programmable gate array. Control circuitry 42 executes a stored program to control the operation of the transmitter circuitry 44 and battery status circuitry 46 and to receive information from these circuits and from the leads 14, which may be transmitted to the base station 50. Battery information from the data lead 31' is provided to battery status circuitry 46 which then may provide a signal to be transmitted by transmitter circuitry 44 wirelessly to a base station 50, as described in U.S. Pat. No. 7,091,879, the disclosure of which is incorporated herein by reference.

Figure 4:
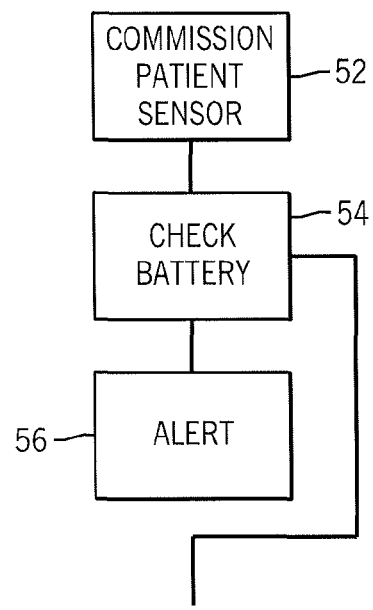
FIG. 4 is a flow chart of a communication synchronization program used by the present invention to ensure reliable operation of the patient monitor incorporating the patient sensor of FIGS. 1-3.

Referring to FIGS. 3 and 4, stored programs executing in the control circuitry 42 and in the base station 50 operate to require a communication synchronization of the patient sensor 10 with the base station 50 indicated by process block 52 prior to use of the patient sensor 10. This communication synchronization process provides a logical mapping of data from the patient sensor 10 to a display portion of the base station 50.

After this communication synchronization, as indicated by process block 54, a check of the battery 20 can be made at the base station 50 that received battery data relayed from the patient sensor 10 to determine that there is sufficient electrical power remaining in the battery 20 to amply complete the scheduled MRI scan. In this regard, the base station 50 may have software to determine a minimal change required for the scheduled MRI scan based on the particulars of the scheduled MRI scan. If the battery of the commissioned patient sensor lacks the necessary charge for the scheduled MRI scan, the operator is signaled as indicated by process block 56 to replace the battery 20 with a freshly charged or new battery 20. By having the base station determine if the commissioned patient sensor has a battery of sufficient charge, an operator is not required to determine the amount of charge that is needed to complete patient monitoring during the scheduling MRI scan. Any replacement of the battery is simplified by the elimination of a possibly cumbersome radio frequency shielding enclosure around the battery 20.

If the battery 20 has sufficient charge, the patient sensor 10 may be used to transmit physiological data. The base station 50 may store the battery usage data to track usage of the batteries 20 to establish their proper maintenance.

Some of the features of the present invention can also be used for other energy storage systems, including, for example, high-capacity capacitors where the capacitor is inserted into similar pocket structure.

It is specifically intended that the present invention not be limited to the embodiments and illustrations contained herein and the claims should be understood to include modified forms of those embodiments including portions of the embodiments and combinations of elements of different embodiments as come within the scope of the following claims.

What is claimed:

1. A wireless patient monitoring system for acquiring and wirelessly transmitting physiological data from a patient undergoing an MRI examination in an MRI machine, comprising:
  a housing;
  leads which acquire the physiological data from the patient during the MRI examination, the leads extending from the housing;
  an antenna which wirelessly transmits physiological data acquired from the patient during an MRI examination, the antenna supported by the housing;
  first and second interior portions defined within the housing, wherein the first interior portion is open to receive outside electrical interference including RF signals from the MRI machine and electrically isolated from the second interior portion;
  RF shielding which RF shields the second interior portion from RF signals from the MRI machine, a portion of the RF shielding extending between the first and second interior portions to RF shield the second interior portion from RF signals received via the first interior portion;
  circuitry disposed in the second interior portion, the circuitry including transmitter circuitry configured to transmit the physiological data wirelessly via the antenna to a remote base station; and
  a battery substantially free from ferromagnetic components and disposed in the first interior portion.

2. The wireless patient monitoring system of claim 1 wherein the battery is a rechargeable battery.

3. The wireless patient monitoring system of claim 2 wherein the rechargeable battery is a lithium ion battery.

4. The wireless patient monitoring system of claim 2 wherein the battery includes integrated circuitry monitoring battery status information that includes at least one of battery type, battery capacity, remaining battery charge, and charge time.

5. The wireless patient monitoring system of claim 4 further comprising:
  an electrical connector formed in the RF shielding portion between the first interior portion and the second interior portion to pass power and battery status from the battery disposed in the first interior portion to the circuitry disposed in the second interior portion;
  wherein the battery has at least two terminals that electrically connect with the connector; and
  an interface having a band pass filter through which the battery status information passes from the connector to the circuitry and a low pass filter through which power passes from the connector to the circuitry.

6. The wireless patient monitoring system of claim 1 further including:
  a connector extending through the RF shielding, the circuit being connected with the connector; and
  an interface between the connector and the circuit, the interface blocking RF energy present on terminals of the battery.

7. The wireless patient monitoring system of claim 6 wherein the housing further includes a chamber RF shielded from the first and second interior portions, the chamber holding the interface.

8. A wireless patient sensor operative within an MRI machine to sense physiological data indicative of at least one of heartbeat, respiration, temperature, and blood oxygen of a patient during an MRI examination, comprising:
  a battery pocket containing a battery, the battery pocket being defined in the housing and open to receive the RF signals generated during the MRI examination;
  an RF shielded circuitry housing portion containing circuitry disposed within an interior volume of the RF shielded circuitry housing such that the circuitry is shielded from receiving RF signals generated during the MRI examination, including RF signals received in the battery pocket; and
  RF signal blocking electrical connections through the RF shielded circuitry housing to electrically connect a ferromagnetic component free battery received in the battery pocket with the circuitry.

9. The wireless patient sensor of claim 8 wherein the housing includes an RF shield.

10. The wireless patient sensor of claim 9 wherein a portion of the RF shield extends between the battery pocket and the housing portion.

11. The wireless patient sensor of claim 8 wherein the circuitry acquires physiological data from the patient during the MRI examination.

12. The wireless patient sensor of claim 11 wherein the circuitry acquires status information of the battery.

13. The wireless patient monitoring system of claim 12 wherein the circuitry includes transmitter circuitry for transmitting the physiological data and the battery status information wirelessly via an antenna exterior to the housing to a remote base station.

14. The wireless patient sensor of claim 12 further including:
  at least one filter that filters a data signal and a power signal provided by the battery to the circuitry.

15. The wireless patient sensor of claim 14 wherein the at least one filter includes filter elements that provide low pass filtering on the power signal from the battery and that provide band pass or lowpass filtering on the data signal from the battery.

16. The wireless patient sensor of claim 15 wherein the at least one filter is contained in a chamber, the chamber including a first electrically conductive interior wall and a second electrically conductive interior wall, a first set of feed through capacitors formed in the first electrically conductive interior wall, and a second set of feed through capacitors formed in the second electrically conductive interior wall, and wherein the at least one filter includes RF chokes disposed between the first set of feed through capacitors and the second set of feed through capacitors.

17. A wireless patient sensor operative with an MRI machine during an MRI examination, comprising:
 a housing having an interior volume;
 a chamber disposed within a first portion of the interior volume and defined by electrically conductive walls;
 a shielded circuitry housing containing circuitry within a second portion of the interior volume;
 a battery pocket containing a battery, the battery pocket being disposed within a third portion of the interior volume, electrically isolated from the chamber, and open to outside electrical interference; and
 electrical connections between the shielded circuitry and the battery pocket through the chamber;
 wherein the circuitry includes transmitter circuitry that wirelessly transmits data to a remote base unit.

18. A method comprising:
 at a commissioned patient sensor having circuitry to acquire physiological signals from a patient during an MRI examination and further having a battery to supply power to the circuitry, determining a charge of the battery;
 performing a communication synchronization of the patient sensor with a base station prior to use of the patient sensor in a scheduled MRI examination;
 with a processor at the base station, determining a minimal charge value required to complete the scheduled MRI examination based on particulars of the scheduled MRI examination;
 with the processor, comparing the determined battery charge of the patient sensor to the minimal charge value for the scheduled MRI examination; and
 wirelessly signaling that the commissioned patient sensor lacks the battery charge required to perform the scheduled MRI examination if the battery charge of the patient sensor is less than the determined minimal charge value.

19. The method of claim 18 further comprising:
 monitoring the battery charge of the patient sensor during the acquisition of physiological signals during the scheduled MRI examination; and
 if the charge of the battery falls below the minimal charge value, wirelessly transmitting a low battery charge signal to the base station.

20. The method of claim 19 further comprising:
 wirelessly transmitting data to the base station associated with physiological signals acquired from the patient.

21. The method of claim 19 further comprising:
 storing battery usage data and determining maintenance needs for the battery from the stored battery usage data.

22. The method of claim 19 further comprising:
 preventing the acquisition of physiological signals if the charge of the battery is below the minimal charge value.

\* \* \* \* \*